United States Patent
Azimpoor

(10) Patent No.: US 12,121,241 B1
(45) Date of Patent: Oct. 22, 2024

(54) CRANIAL DRILL GUARDS, STABILIZERS AND METHODS OF USING THE SAME

(71) Applicant: Ali F. Azimpoor, Houston, TX (US)

(72) Inventor: Ali F. Azimpoor, Houston, TX (US)

(73) Assignee: Ali F. Azimpoor, Houston, TX (US)

( * ) Notice: Subject to any disclaimer, the term of this patent is extended or adjusted under 35 U.S.C. 154(b) by 0 days.

(21) Appl. No.: 18/370,059

(22) Filed: Sep. 19, 2023

(51) Int. Cl.
*A61B 17/16* (2006.01)

(52) U.S. Cl.
CPC ...... *A61B 17/1617* (2013.01); *A61B 17/1695* (2013.01)

(58) Field of Classification Search
CPC ............ A61B 17/1617; A61B 17/1695
See application file for complete search history.

(56) References Cited

U.S. PATENT DOCUMENTS

| | | | |
|---|---|---|---|
| 4,646,752 A | 3/1987 | Swann et al. | |
| 4,931,056 A | 6/1990 | Ghajar et al. | |
| 5,382,250 A | 1/1995 | Kraus et al. | |
| 5,876,405 A * | 3/1999 | Del Rio | A61B 17/1695 606/80 |
| 6,152,933 A * | 11/2000 | Werp | A61M 27/006 604/165.01 |
| 6,206,885 B1 | 3/2001 | Ghahremani et al. | |
| 6,382,250 B1 | 5/2002 | Gruschwitz et al. | |
| 6,702,818 B2 | 3/2004 | Kupferschmid et al. | |
| 8,152,809 B1 * | 4/2012 | Kao | A61B 17/1695 408/202 |
| 9,226,732 B2 | 1/2016 | Azimpoor et al. | |
| 10,695,001 B2 | 6/2020 | Bobo et al. | |
| 2004/0034382 A1 * | 2/2004 | Thomas | A61B 17/1695 606/180 |
| 2010/0034605 A1 | 2/2010 | Huckins et al. | |
| 2013/0131546 A1 | 5/2013 | Azimpoor et al. | |
| 2015/0127040 A1 | 5/2015 | Gill et al. | |

(Continued)

FOREIGN PATENT DOCUMENTS

| | | |
|---|---|---|
| CN | 107951533 B | 6/2019 |
| CN | 211270984 U | 8/2020 |

(Continued)

OTHER PUBLICATIONS

Ito M, Sonokawa T, Mishina H, Sato K. Penetrating injury of the brain by the burr of a high-speed air drill during craniotomy: case report. J Clin Neurosci. May 2001;8(3):261-3. doi: 10.1054/jocn.1999.0733. PMID: 11386803.

(Continued)

*Primary Examiner* — Kevin T Truong
*Assistant Examiner* — Diana Jones
(74) *Attorney, Agent, or Firm* — Shackelford, McKinley & Norton, LLP

(57) ABSTRACT

A cranial drill guard operational for stabilizing a cranial drill bit, where the cranial drill guard includes: a proximal end with a proximal surface operational to receive the cranial drill bit; a distal end with a distal surface operational to interface with a skull bone, and a plurality of protruding ridges for attachment to the skull bone; a wall extending from the proximal end to the distal end; and a cavity within the wall, where the cavity extends longitudinally from the proximal end to the distal end and is operational to stabilize and guard the cranial drill bit. The wall may include one or more apertures that extend through the wall. Additional embodiments pertain to methods of perforating a skull bone of a cranium of a subject by utilizing the cranial drill guard.

25 Claims, 7 Drawing Sheets

(56) References Cited

U.S. PATENT DOCUMENTS

| | | | |
|---|---|---|---|
| 2018/0206883 A1* | 7/2018 | McIntyre | ............ A61B 17/3423 |
| 2021/0113220 A1 | 4/2021 | Putz et al. | |
| 2021/0346061 A1 | 11/2021 | Zille | |
| 2023/0157705 A1 | 5/2023 | Reynolds | |

FOREIGN PATENT DOCUMENTS

| | | | | |
|---|---|---|---|---|
| CN | 213606675 U | | 7/2021 | |
| CN | 113413188 A | | 9/2021 | |
| CN | 113974762 A | * | 1/2022 | |
| EP | 1849418 A1 | * | 10/2007 | ......... A61B 17/1635 |
| WO | WO2020133231 | | 7/2020 | |

OTHER PUBLICATIONS

Caird et al., 'Plunging' during burr hole craniostomy: a persistent problem amongst neurosurgeons in Britain and Ireland, British Journal of Neurosurgery, Dec. 2003; 17 (6): 509-512.

Vogel TW, Dlouhy BJ, Howard MA 3rd. Don't take the plunge: avoiding adverse events with cranial perforators. J Neurosurg. Sep. 2011;115(3):570-5. doi: 10.3171/2011.3.JNS101310. Epub Apr. 1, 2011. PMID: 21456895.

Jennifer Whitlock, RN, MSN, FN, "Burr Hole Surgery", Very Well Health, Jan. 9, 2020 (obtained from https://www.verywellhealth.com/burr-hole-surgery-information-3157273?print).

Maria Cohut, Ph.D., Skull-drilling: The ancient roots of modern neurosurgery, Medical News Today, Jun. 12, 2018 (obtained from https://www.medicalnewstoday.com/articles/322109).

Codman Surgical Product Catalog for "CODMAN Cervical Drill Guards, with bone relief, and four pins." Catalog Nos. 12-1005 and 12-1006. Obtained from https://www.surgicalholdings.co.uk/media/files/codman%20cat.pdf on Sep. 6, 2023.

Limbu et al. "Incidence of Dural Injury during Craniotomy—a Single Center Study." egneuro,02(02):57-60,2020.

Kenny Koehler. "History of the Power Drill: a Beginner's Guide to a Popular Tool", Jul. 9, 2021, Protool Reviews. Downloaded from: https://www.protoolreviews.com/what-is-a-drill/.

* cited by examiner

CRANIAL DRILL GUARDS, STABILIZERS AND METHODS OF USING THE SAME

BACKGROUND

Current devices for preventing cranial drill bit plunging and imperfect perforation during brain surgery have numerous limitations. Embodiments of the present disclosure aim to address the root cause of such limitations.

SUMMARY

In some embodiments, the present disclosure pertains to a cranial drill guard that is operational for stabilizing a cranial drill bit. In some embodiments, the cranial drill guard includes: a proximal end with a proximal surface, where the proximal end is operational to receive the cranial drill bit; a distal end with a distal surface operational to interface with a skull bone, and a plurality of protruding ridges for attachment to the skull bone; a wall extending from the proximal end to the distal end; and a cavity within the wall, where the cavity extends longitudinally from the proximal end to the distal end, and where the cavity is operational to stabilize and guard the cranial drill bit.

In some embodiments, the diameter of the proximal surface is larger than the diameter of the cavity. In some embodiments, the proximal surface is operational to guide the cranial drill bit into the cavity.

In some embodiments, the diameter of the distal surface is larger than the diameter of the cavity. In some embodiments, the distal surface includes a concave surface.

In some embodiments, the plurality of protruding ridges protrude out of the distal surface. In some embodiments, the plurality of protruding ridges are in the form of a plurality of protruding spikes that protrude out of the distal surface. In some embodiments, the plurality of protruding ridges are in the form of a plurality of protruding helical ridges that protrude out of the wall of the distal end. In some embodiments, the plurality of protruding helical ridges are in the form of threads, ultrathin threads, serrations, screws, or combinations thereof.

In some embodiments, the wall of the cranial drill guard includes one or more apertures that extend through the wall. In some embodiments, the one or more apertures are operational to at least dispense skull bone components (e.g., skull bone fragments and/or skull bone dust), allow irrigation during drilling, mitigate overheating of the cranial drill bit and cranial drill guard, and/or mitigate jamming of the cranial drill bit and cranial drill guard.

Additional embodiments of the present disclosure pertain to methods of perforating the skull bone of a cranium of a subject by placing a cranial drill guard of the present disclosure on the skull bone of the subject; attaching the plurality of protruding ridges of the cranial drill guard to the skull bone of the subject; inserting the cranial drill bit into the cavity of the cranial drill guard; and actuating the cranial drill bit to perforate the skull bone. In some embodiments, the cavity guards and stabilizes the cranial drill bit during the actuating.

In some embodiments where the plurality of protruding ridges of the cranial drill guard are in the form of a plurality of protruding spikes, the attachment step may include pushing the plurality of spikes into the skull bone of the subject. In some embodiments where the plurality of protruding ridges of the cranial drill guard are in the form of a plurality of protruding helical ridges, the attachment may include screwing the plurality of protruding helical ridges into the skull bone of the subject.

DETAILED DESCRIPTION

Figure 1A:
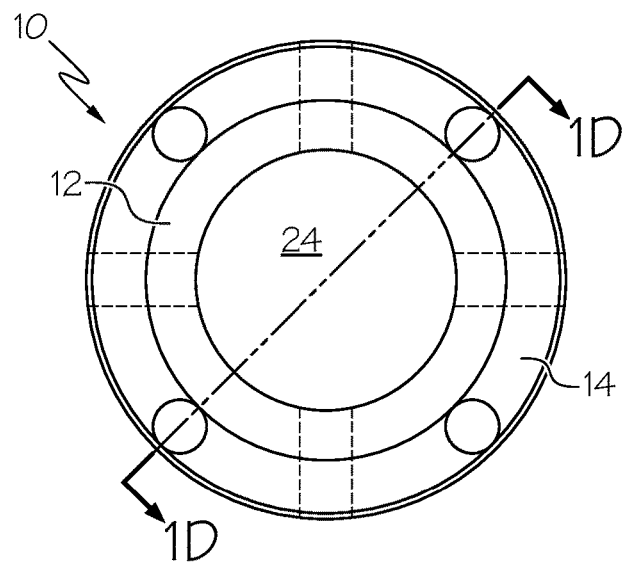
FIGS. 1A-1K illustrate an embodiment of a cranial drill guard and its operation.
Figure 1B:
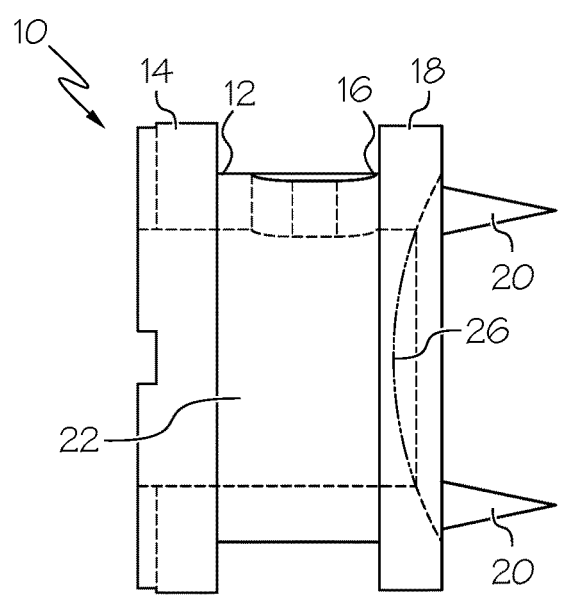
Figure 1C:
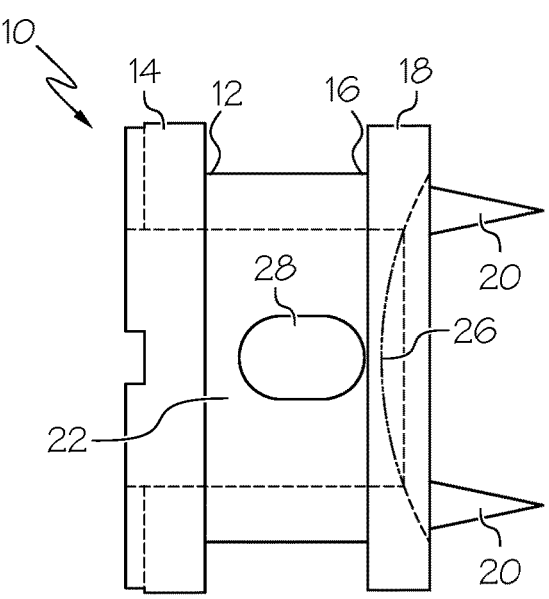
Figure 1D:
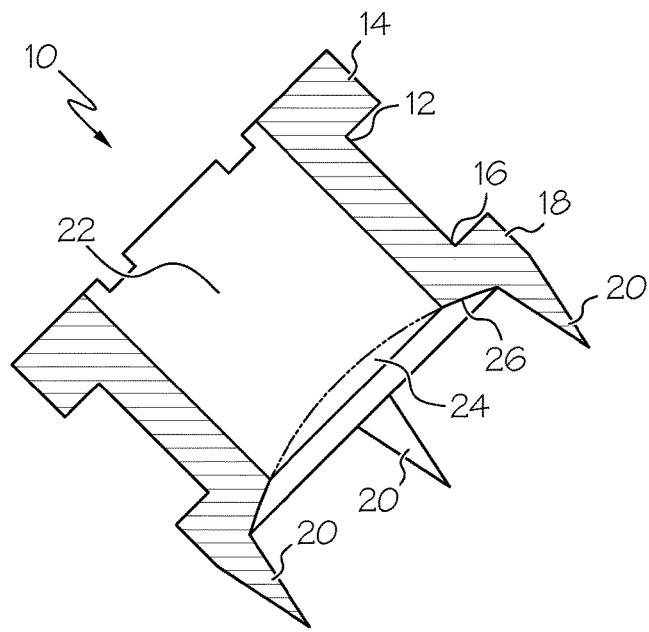
Figure 1E:
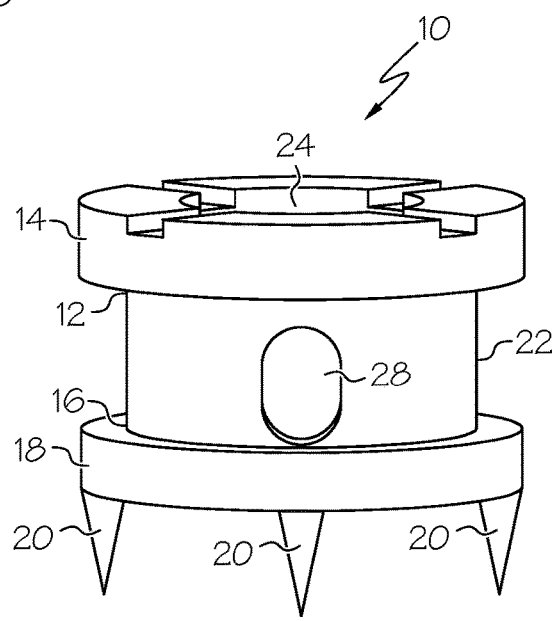
Figure 1F:
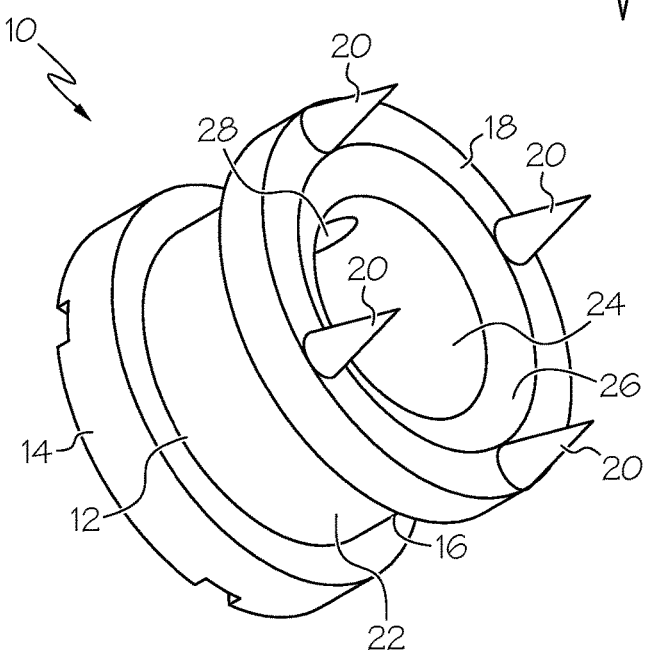

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

The human skull bone houses and protects the cranium from outside forces. Skull bones include eight bones joined tightly through fibrous sutures. Skull bones are very resilient and can withstand forces of up to 6.5 Gpa before fracturing.

A cross section of skull bones show different layers. Such layers include the periosteum layer, a shiny, strong and slippery dense layer of vascular connective tissue covering the outer table of skull; the outer table, a layer of strong and dense compact bone; a spongy bony material between outer and inner tables of the skull; and an inner table similar to outer table of skull.

To perform brain surgery, skull bones must be penetrated. Neurosurgeons may initially choose a burr site, make a small scalp incision on the selected burr site, and then place a retractor that exposes the periosteum (i.e., a sheet outside the skull bone that supplies the skull bone with blood, nerves, and cells). A high speed automatic release drill with a cranial drill bit may then be checked for functionality and brought into contact with the periosteum.

Often, a cranial drill bit used for penetrating skull bones may slip due to the smoothness of the periosteum and the uneven surface of the skull bone. Many times, such slips result in scalp laceration.

Once a drill is engaged with a skull bone, the drill should preferably stay perpendicular to the skull bone until a hole is made. However, such a practice may be disregarded by neurosurgeons, thereby resulting in the plunging of the drill into the brain and/or partial perforation. Such plunging can result in surgical complications, such as dural lacerations, cortical contusions, and/or tearing of one or more bridging veins.

In fact, plunging is prevalent among neurosurgeons. For instance, an anonymous survey of British and Irish neurosurgeons showed that 65% of the neurosurgeons experienced plunging at least once while 22% of them experienced plunging at least twice. Moreover, the survey revealed that 78% of the plunging involved senior trainees while 22% of the plunging involved faculty members.

The prevalence of plunging is further reflected by the high global rates of brain surgery. For instance, According to the American Association of Neurological Surgeons, 13.8 million craniotomies are performed in the US annually by about 5,000 neurosurgeons.

Plunging and incomplete perforation can have numerous causes. Such causes can include, without limitation, use and misuse of pneumatic high speed drill bits, poor training of a surgeon (e.g., drilling with one hand without the support of the other), sudden surge of torque by a high speed pneumatic drill, fatigue of the operator, ricocheting off of a drill bit during surgery, removal of the drill to check the depth of the hole, not maintaining a perpendicular angle of the drill during perforation, rotating the drill during perforation, inadequate irrigation that results in overheating and malfunctioning of the drill, and most importantly lack of protective stabilizing drill guards.

Numerous devices have been developed to prevent plunging during brain surgery. However, such devices suffer from various limitations. For instance, many protective devices do not have any built-in measures to dispose bone dust while drilling. As such, many devices may overheat or jam during drilling. Many protective devices may also be impractical for surgical use due to structural instability, bulkiness, costliness, non-reusability, and lack of mechanisms for guarding and stabilizing a drill bit during contact.

As such, a dire need exists for the development of protective devices that guard and maintain the stability of cranial drills bit during brain surgery. Numerous embodiments of the present disclosure aim to address the aforementioned need.

Cranial Drill Guards

In some embodiments, the present disclosure pertains to cranial drill guards that are operational for stabilizing a cranial drill bit. As set forth in more detail herein, the cranial drill guards of the present disclosure can have various structures and arrangements.

Figure 1G:
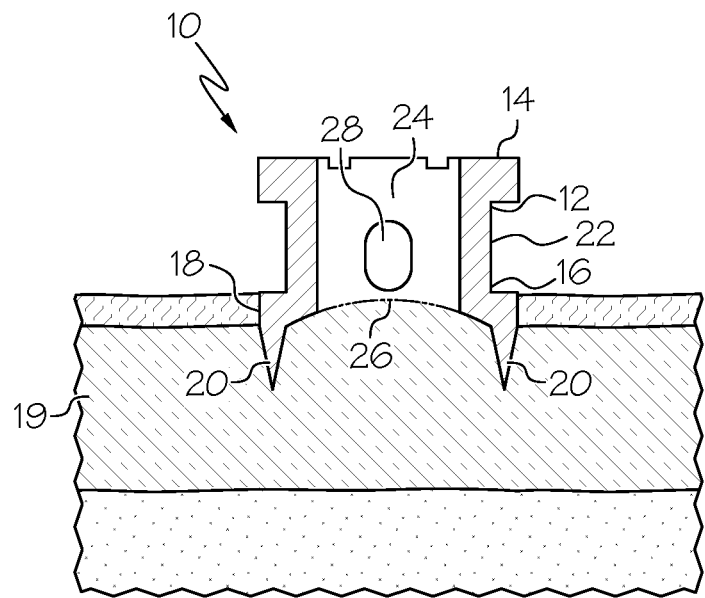
Figure 1H:
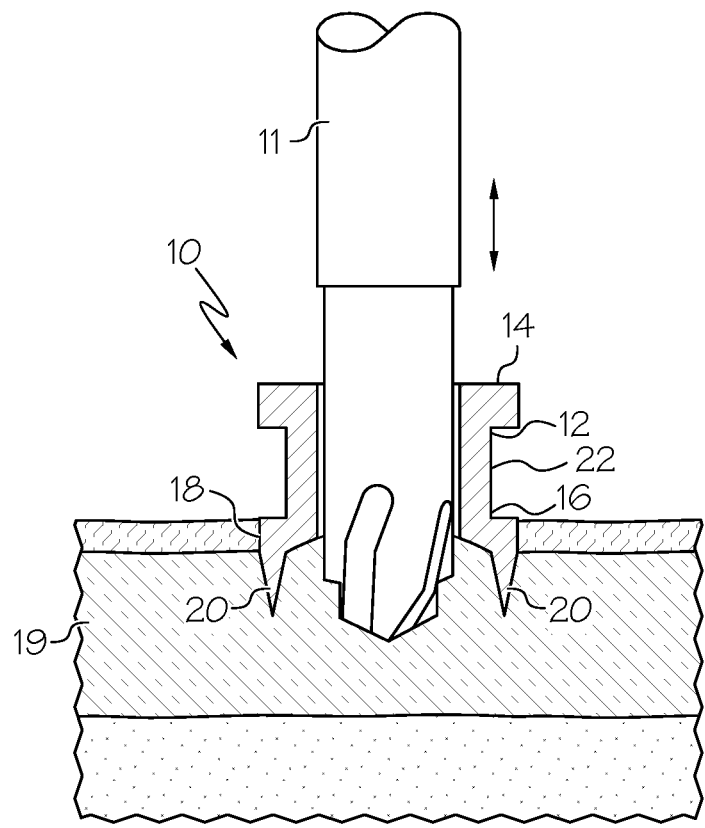

An example of a cranial drill guard of the present disclosure is illustrated in FIGS. 1A-1I as cranial drill guard 10. Cranial drill guard 10 includes a proximal end 12 with a proximal surface 14. As illustrated in FIG. 1H, proximal end 12 is operational to receive a cranial drill bit 11.

Figure 1I:
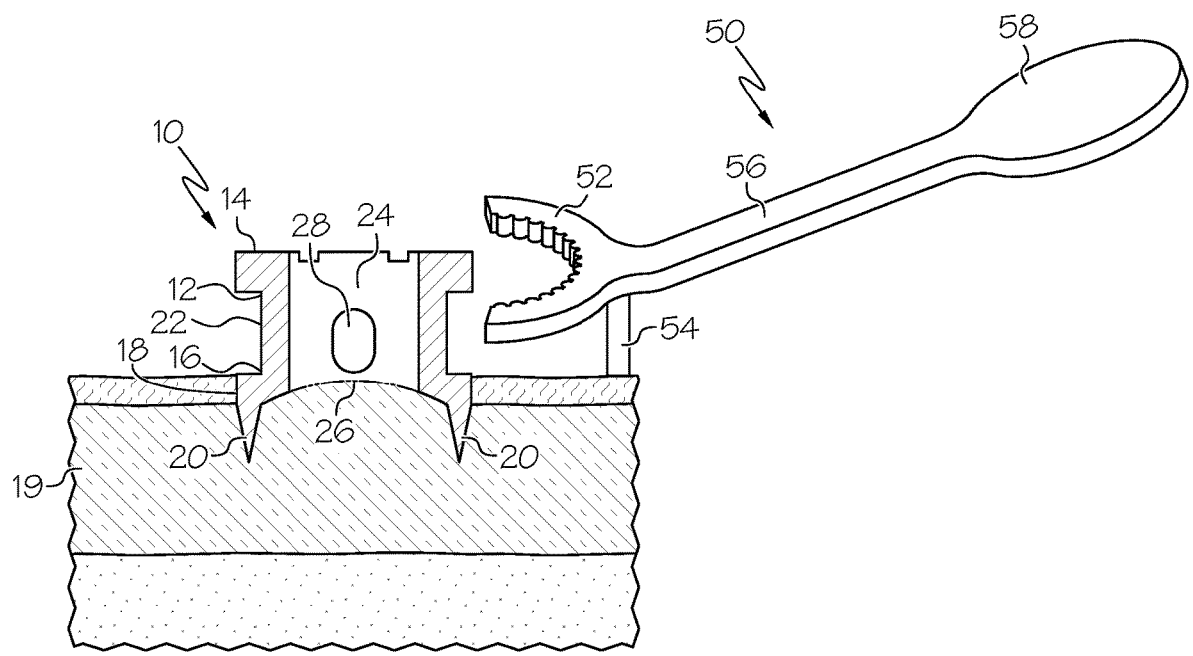

Cranial drill guard 10 also includes a distal end 16 with a distal surface 18. As illustrated in FIGS. 1G-1I, distal surface 18 is operational to interface with a skull bone 19. Distal end 16 also includes a plurality of protruding ridges 20 for attachment to skull bone 19. As further illustrated in FIGS. 1B-1I, distal surface 18 includes a concave surface 26 that is operational to accommodate the convexity of the skull bone. In particular, concave surface 26 in this example has a 5 degree concavity to accommodate various convexities of skull bone surfaces.

Additionally, cranial drill guard 10 includes a wall 22 that extends from proximal end 12 to distal end 16. Wall 22 also includes an aperture 28 that extends through the wall. Aperture 28 is operational to at least dispense skull bone components (e.g., skull bone fragments and/or skull bone dust), allow irrigation during drilling, mitigate overheating of cranial drill bit 11 and cranial drill guard 10, and/or mitigate jamming of the cranial drill bit 11 and cranial drill guard 10.

Cranial drill guard 10 also includes a cavity 24 within wall 22 that extends longitudinally from proximal end 12 to distal end 16. Cavity 24 is operational to stabilize and guard cranial drill bit 11.

Figure 1J:
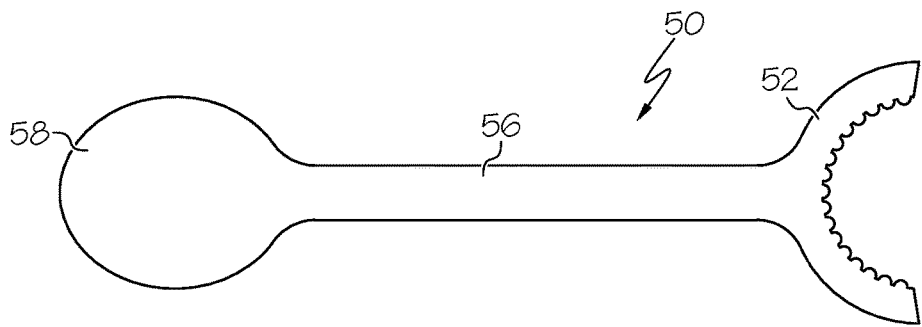
Figure 1K:
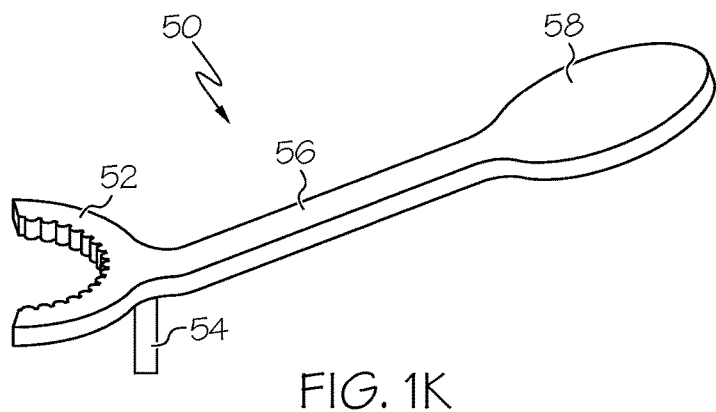

As illustrated in FIGS. 1I-1K, cranial drill guard 10 may be associated with guard actuator 50 that is operational to remove cranial drill guard 10 from skull bone 19. Guard actuator 50 includes grasper 52 operational for grasping proximal surface 14, stabilizer 54 operational for associating with skull bone 19, a user handle 58, and a lever 56 positioned between grasper 52 and user handle 58.

Figure 2A:
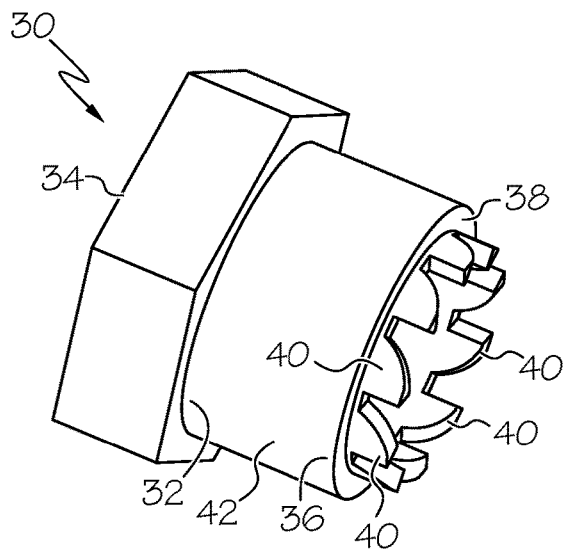
FIGS. 2A-2F illustrate an alternative embodiment of a cranial drill guard and its operation.
Figure 2B:
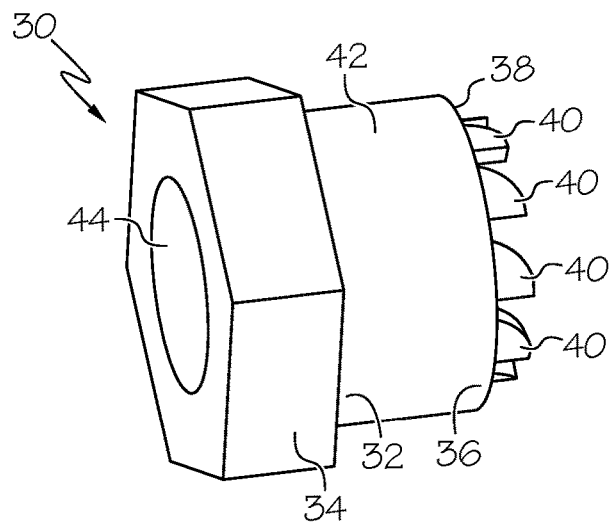
Figure 2C:
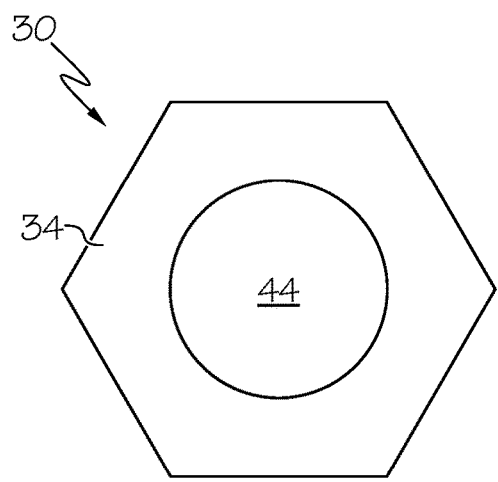
Figure 2D:
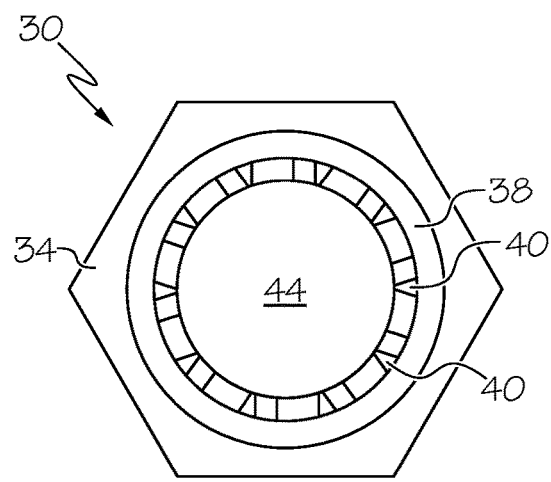
Figure 2E:
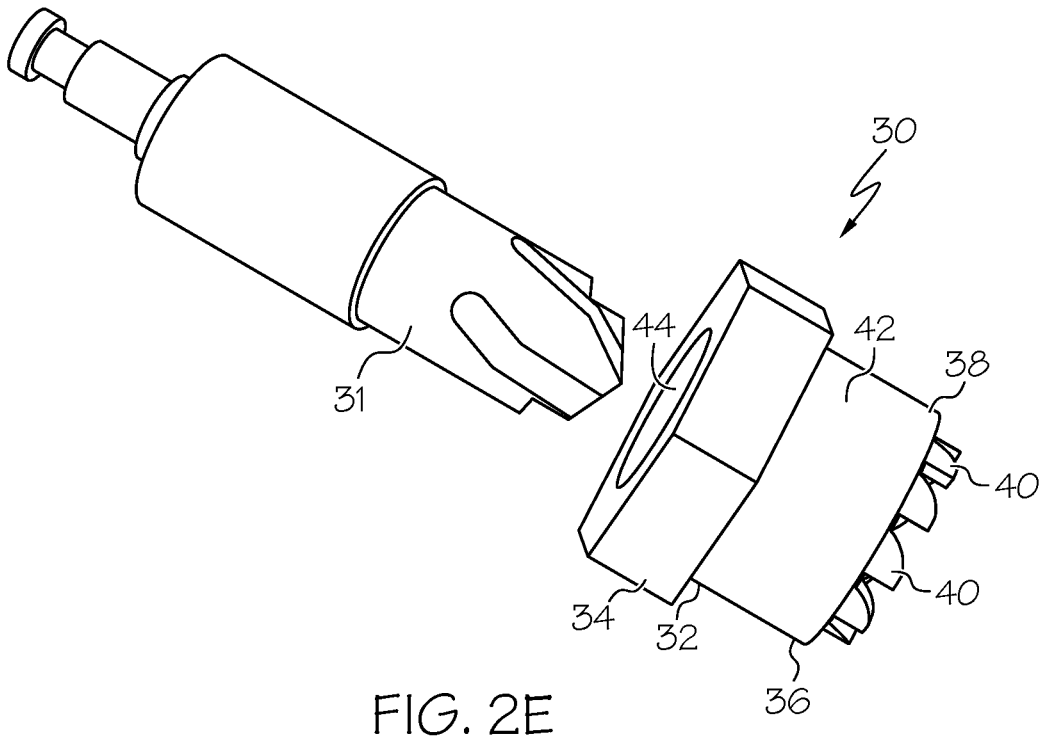
Figure 2F:
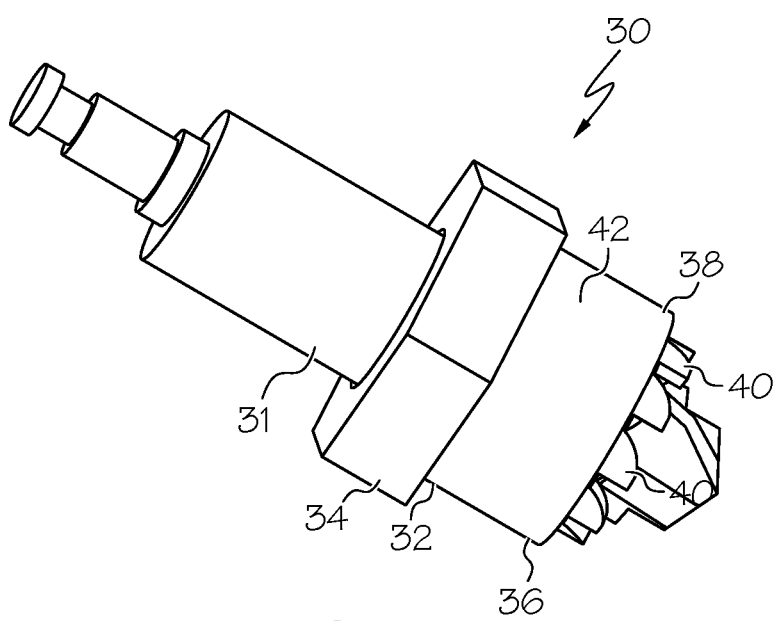

An additional example of a cranial drill guard of the present disclosure is illustrated in FIGS. 2A-2F as cranial drill guard 30. Cranial drill guard 30 includes a proximal end 32 with a proximal surface 34. As illustrated in FIGS. 2E-2F, proximal end 32 is operational to receive a cranial drill bit 31.

Cranial drill guard 30 also includes a distal end 36 with a distal surface 38 that is operational to interface with a skull bone. Distal end 36 also includes a plurality of protruding ridges 40 for attachment to a skull bone.

Additionally, cranial drill guard 30 includes a wall 42 that extends from proximal end 32 to distal end 36. Cranial drill guard 30 also includes a cavity 44 within wall 42 that extends longitudinally from proximal end 32 to distal end 36. Cavity 44 is operational to stabilize and guard cranial drill bit 31.

Figure 3A:
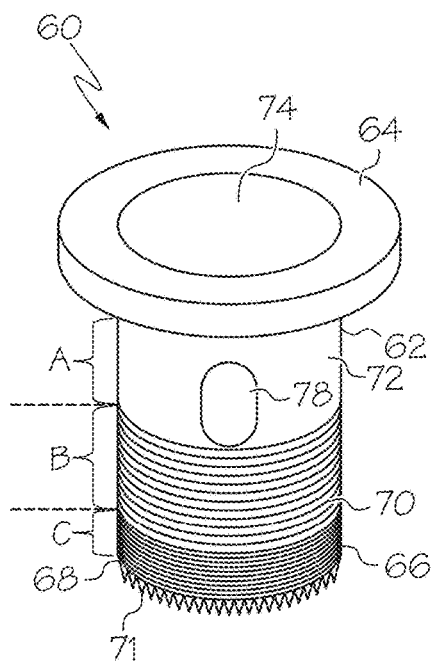
FIGS. 3A-3C illustrate another alternative embodiment of a cranial drill guard and its operation.
Figure 3B:
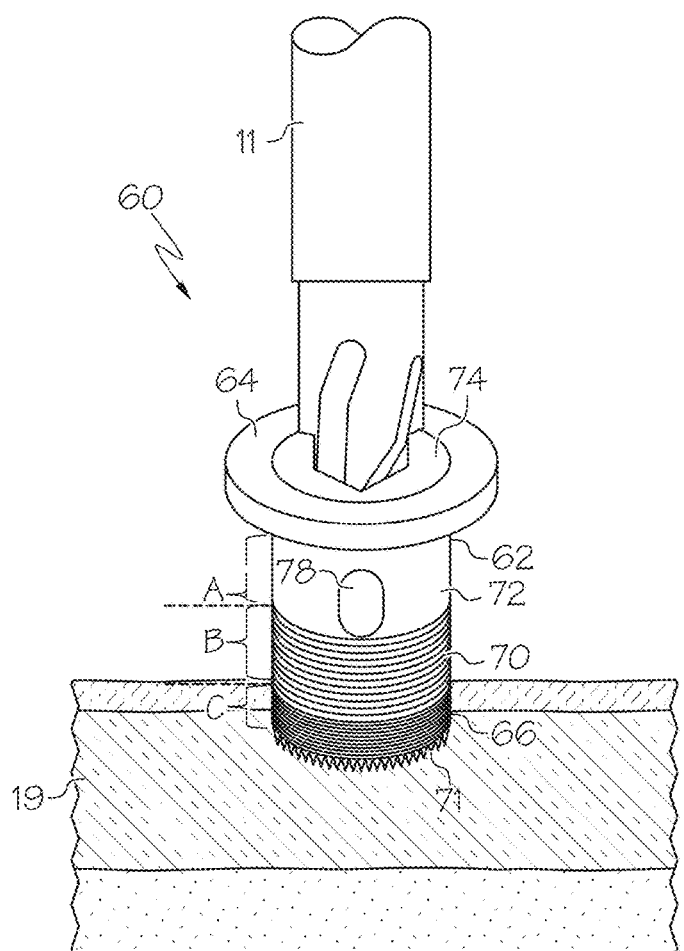

An additional example of a cranial drill guard of the present disclosure is illustrated in FIGS. 3A-3B as cranial drill guard 60. Cranial drill guard 60 includes a proximal end 62 with a proximal surface 64. As illustrated in FIG. 3B, proximal end 62 is operational to receive a cranial drill bit 11.

Cranial drill guard 60 also includes a distal end 66 with a distal surface 68 that is operational to interface with a skull bone. Additionally, cranial drill guard 60 includes a wall 72 that extends from proximal end 62 to distal end 66. Wall 72 generally includes regions A, B and C. Cranial drill guard 60 also includes a cavity 74 within wall 72 that extends longitudinally from proximal end 62 to distal end 66. Cavity 74 is operational to stabilize and guard cranial drill bit 11.

Wall 72 also includes an aperture 78 that extends through the wall. Aperture 78 is operational to at least dispense skull bone components (e.g., skull bone fragments and/or skull bone dust), allow irrigation during drilling, mitigate overheating of cranial drill bit 11 and cranial drill guard 60, and/or mitigate jamming of the cranial drill bit 11 and cranial drill guard 60.

Cranial drill guard 60 also includes a plurality of protruding helical ridges 70 that protrude out of regions B and C of wall 72, which is proximal to distal end 66. In this example, the plurality of protruding helical ridges 70 are in the form of threads that form a screw-like structure. Additionally, the plurality of helical ridges 70 in region C of wall 72 include thinner threads than the plurality of helical ridges 70 in region B of wall 72. For instance, in some embodiments, the plurality of helical ridges 70 in region C of wall 72 include ultrathin threads and the plurality of helical ridges 70 in region B of wall 72 include thin threads. However, region A of wall 72 remains devoid of any helical ridges. In some embodiments, regions A and B each have a length of about 10 mm while region C has a length of about 5 mm.

Distal end 66 also includes a plurality of serrations 71 for attachment to a skull bone. In this example, serrations 71 protrude out of distal surface 68. In some embodiments, the serrations have a length of approximately 1 mm.

Figure 3C:
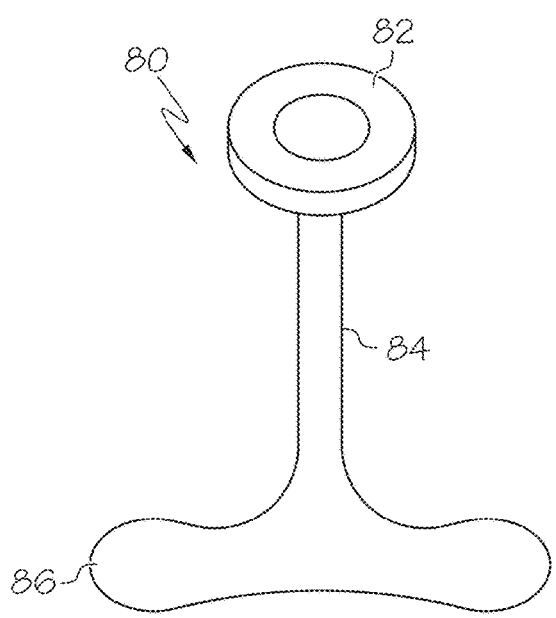

As illustrated in FIG. 3C, cranial drill guard 60 may be associated with guard actuator 80 that is operational to attach and remove cranial drill guard 60 from skull bone 19. Guard actuator 80 includes grasper 82 operational for grasping proximal surface 64, a user handle 86, and a lever 84 positioned between grasper 82 and user handle 86.

The proximal ends and proximal surfaces of the cranial drill guards of the present disclosure can have various structures and dimensions. For instance, in some embodiments, the diameter of the proximal surface of a cranial drill guard is larger than the diameter of the cavity (e.g., proximal surfaces 14, 34, and 64 in FIGS. 1A-1I, 2A-2F, and 3A-3B, respectively). In some embodiments, the proximal surface includes a rim (e.g., rims 14, 34 and 64 in FIGS. 1A-11, 2A-2F, and 3A-3B, respectively). In some embodiments, the proximal surface is operational to guide the cranial drill bit into the cavity.

The cranial drill guards of the present disclosure may have various lengths. For instance, in some embodiments, the distance between the proximal end and distal end of a cranial drill guard is less than about 100 mm. In some embodiments, the distance between the proximal end and distal end is less than about 80 mm. In some embodiments, the distance between the proximal end and distal end is less than about 75 mm. In some embodiments, the distance between the proximal end and distal end is less than about 60 mm. In some embodiments, the distance between the proximal end and distal end is less than about 50 mm. In some embodiments, the distance between the proximal end and distal end is less than about 30 mm. In some embodiments, the distance between the proximal end and distal end is less than about 20 mm. In some embodiments, the distance between the proximal end and distal end is less than about 15 mm.

In some embodiments, the distance between the proximal end and distal end is about 25 mm. In some embodiments, the distance between the proximal end and distal end is about 15 mm.

The distal ends and distal surfaces of the cranial drill guards of the present disclosure can also have various structures and dimensions. For instance, in some embodiments, the diameter of the distal surface is larger than the diameter of the cavity (e.g., distal surface 18 in FIGS. 2A-2F). In some embodiments, the distal surface is in the form of a plate, such as a foot plate (e.g., foot plates 18 and 38 in FIGS. 1A-1I and 2A-2F, respectively). In some embodiments, the distal surface also includes a concave surface (e.g., concave surface 26 in FIGS. 1B-1I). In some embodiments, the concave surface is operational to accommodate the convexity of a skull bone.

The cranial drill guards of the present disclosure can include a plurality of protruding ridges. Protruding ridges generally refer to structures that protrude out of a distal end of a cranial drill guard, and that are operational to attach to a skull bone. In some embodiments, the protruding ridges engage the skull bone and help stabilize the cranial drill guard on the skull bone. In some embodiments, the protruding ridges protrude out of a distal surface of a cranial drill guard. In some embodiments, the protruding ridges protrude out of a wall of a distal end.

In some embodiments, the plurality of protruding ridges are in the form of a plurality of protruding spikes (e.g., spikes 20 and 40 shown in FIGS. 1A-1I and FIGS. 2A-2F, respectively). In some embodiments, the plurality of protruding spikes protrude out of the distal surface (e.g., distal surfaces 18 and 38 shown in FIGS. 1A-1I and FIGS. 2A-2F, respectively). In some embodiments, at least four spikes protrude out of a foot plate of a cranial guard's distal surface (e.g., spikes 20 protruding out of foot plate 18 shown in FIGS. 1A-1I).

In some embodiments, the plurality of protruding ridges of a cranial drill guard are in the form of a plurality of protruding helical ridges (e.g., protruding helical ridges 70 shown in FIGS. 3A-3B). In some embodiments, the plurality of protruding helical ridges protrude out of the wall of the distal end of a cranial drill guard (e.g., protruding helical ridges 70 protruding out of wall 72, as shown in FIGS. 3A-3B). In some embodiments, the plurality of protruding helical ridges are in the form of threads. In some embodiments, the plurality of protruding helical ridges are in the form of ultrathin threads. In some embodiments, the plurality of protruding helical ridges are in the form of serrations (e.g., serrations 71 shown in FIG. 3A). In some embodiments, the plurality of protruding helical ridges are in the form of a screw.

The cranial drill guards of the present disclosure can include various walls that extend from a distal end to a proximal end. In some embodiments, the wall extends throughout the cranial drill guard to form an outer layer of the cranial drill guard. In some embodiments, the wall is in the shape of a cylinder. In some embodiments, the wall is in the shape of a sleeve. In some embodiments, the wall is in circular form. In some embodiments, the wall has a thickness of at least 1 mm. In some embodiments, the wall has a thickness of at least 2 mm.

In some embodiments, the walls of a cranial drill guard include one or more apertures (e.g., apertures 28 and 78 shown in FIGS. 1C-1I, and FIGS. 3A-3B, respectively). In some embodiments, the one or more apertures extend through a wall. In some embodiments, the wall includes at least two apertures that extend through the wall. In some embodiments, the one or more apertures are operational to at least dispense skull bone components (e.g., skull bone fragments and/or skull bone dust), allow irrigation during drilling, mitigate overheating of the cranial drill bit and cranial drill guard, and/or mitigate jamming of the cranial drill bit and cranial drill guard. For instance, in some embodiments, the one or more apertures allow for irrigation and suction of bone dust during cranial drilling.

The apertures of the present disclosure can have various diameters. For instance, in some embodiments, the apertures include diameters that range from about 1 mm to about 10 mm. In some embodiments, the apertures include diameters that range from about 3 mm to about 8 mm. In some embodiments, the apertures include diameters of at least about 3 mm.

The cranial drill guards of the present disclosure can also include various types of cavities. Such cavities generally extend longitudinally from a proximal end to a distal end of a cranial drill guard. In some embodiments, the cavity is circular. In some embodiments, the cavity has the same diameter from the proximal end to the distal end. In some embodiments, the cavity is operational to stabilize a cranial drill bit and avoid lateral movement of the cranial drill bit.

The cavities of the present disclosure can have various diameters. For instance, in some embodiments, the cavity includes a diameter of at least 5 mm. In some embodiments, the cavity includes a diameter of at least 9 mm. In some embodiments, the cavity includes a diameter of at least 10 mm. In some embodiments, the cavity includes a diameter of at most 20 mm. In some embodiments, the cavity includes a diameter ranging from about 5 mm to about 20 mm. In some embodiments, the cavity includes a diameter ranging from about 9 mm to about 15 mm. In some embodiments, the cavity includes a diameter of about 14 mm to about 15 mm for adult use. In some embodiments, the cavity includes a diameter of about 15 mm for adult use. In some embodiments, the cavity includes a diameter of about 9 mm to about 11 mm for pediatric use. In some embodiments, the cavity includes a diameter of about 10 mm for pediatric use.

The cranial drill guards of the present disclosure can also have various length to diameter ratios. For instance, in some embodiments, the ratio of the distance between the proximal end and distal end and the cavity diameter is less than 5. In some embodiments, the ratio of the distance between the proximal end and distal end and the cavity diameter is less than 4. In some embodiments, the ratio of the distance between the proximal end and distal end and the cavity diameter is less than 3. In some embodiments, the ratio of the distance between the proximal end and distal end and the cavity diameter is less than 2. In some embodiments, the ratio of the distance between the proximal end and distal end and the cavity diameter is about 1.

The cranial drill guards of the present disclosure can have various modes of operation. For instance, in some embodiments, the cranial drill guards of the present disclosure may be operational to receive, stabilize, and guard the cranial drill bit from over-penetration, under-penetration, or incomplete perforation into a subject's skull bone. In some embodiments, the cranial drill guards of the present disclosure maintain a perpendicular position of a cranial drill bit. In some embodiments, the cranial drill guards of the present disclosure are suitable for use in perforating a skull bone of a cranium of a subject. In some embodiments, the cranial drill guards of the present disclosure are suitable for use in performing craniotomy.

Methods of Perforating Skull Bone

Additional embodiments of the present disclosure pertain to methods of perforating a skull bone of a cranium of a subject by utilizing the cranial drill guards of the present disclosure. In some embodiments, the methods of the present disclosure include placing a cranial drill guard of the present disclosure on the skull bone of the subject; attaching the plurality of protruding ridges of the cranial drill guard to the skull bone of the subject; inserting a cranial drill bit into the cavity of the cranial drill guard; and actuating the cranial drill bit to perforate the skull bone. In some embodiments, the cavity guards and stabilizes the cranial drill bit during the actuating.

In some embodiments, the methods of the present disclosure may also include an additional step of removing the cranial drill guard from the skull bone. In some embodiments, the removal occurs after the perforation is completed.

The methods of the present disclosure can have numerous embodiments. For instance, in some embodiments, attachment of the plurality of protruding ridges of the cranial drill guard to the skull bone of a subject includes pushing the plurality of ridges into the skull bone of the subject. In some embodiments, attachment of the plurality of protruding ridges of the cranial drill guard to the skull bone of a subject includes tapping the plurality of ridges into the skull bone of the subject. In some embodiments, such modes of attachment may be suitable for cranial drill guards with a plurality of protruding ridges that are in the form of a plurality of protruding spikes.

In some embodiments, attachment of the plurality of protruding ridges of the cranial drill guard to the skull bone of a subject includes screwing the plurality of ridges into the skull bone of the subject. In some embodiments, such modes of attachment may be suitable for cranial drill guards with a plurality of protruding ridges that are in the form of a plurality of protruding helical ridges, such as threads, ultra-thin threads, serrations, and/or screws.

In some embodiments, the methods of the present disclosure also include a step of selecting a cranial drill guard. In some embodiments, the selection is based on various criteria, such as the age of the patient, and the desired size of a skull bone to be perforated.

In some embodiments, the proximal surface of the cranial drill guard guides the cranial drill bit into the cavity. In some embodiments, the distal surface includes a concave surface that is operational to interface with convex areas of the skull bone.

In some embodiments, the wall of a cranial drill guard includes one or more apertures that extend through the wall. In some embodiments, the one or more apertures are operational to at least dispense skull bone components (e.g., skull bone fragments and/or skull bone dust), allow irrigation during drilling, mitigate overheating of the cranial drill bit and cranial drill guard, and/or mitigate jamming of the cranial drill bit and cranial drill guard.

In some embodiments, the cavity of a cranial drill guard is operational to stabilize the cranial drill bit and avoid lateral movement of the cranial drill bit. In some embodiments, the cranial drill guard is operational to receive, stabilize, and guard the cranial drill bit from over-penetration, under-penetration, or incomplete perforation into the subject's skull bone. For instance, in some embodiments, the proximal surface of the cranial drill guard has a structure that is operational to guard the cranial drill bit from over-penetration, under-penetration, or incomplete perforation into the subject's skull bone (e.g., proximal surfaces 14, 34, and 64, as shown in FIGS. 1A-1I, 2A-2F, and 3A-3B, respectively).

The methods of the present disclosure can have various modes of operation. For instance, in some embodiments illustrated in FIGS. 1G and 1H, the methods of the present disclosure include placing cranial drill guard 10 on skull bone 19 of a subject; attaching the plurality of spikes 20 to skull bone 19 by tapping cranial drill guard 10 onto the skull bone by a lightweight mallet; inserting cranial drill bit 11 into cavity 24 of cranial drill guard 10; and actuating the cranial drill bit to perforate the skull bone. Advantageously, the penetration of cranial drill bit 11 into skull bone 19 stops automatically once cranial drill bit 11 reaches the end of skull bone 19. In some embodiments, the automatic stopping may be actuated by proximal surface 14. Additionally, aperture 28 dispenses skull bone components (e.g., skull bone fragments and/or skull bone dust), allows irrigation during drilling, mitigates overheating of cranial drill bit 11 and cranial drill guard 10 during drilling, and/or mitigates jamming of the cranial drill bit 11 and cranial drill guard 10.

In some embodiments illustrated in FIGS. 1I-IK, cranial drill guard 10 may be removed from skull bone 19 after the perforation is completed through the utilization of guard actuator 50. For instance, in some embodiments, a user may grasp handle 58, place grasper 52 around proximal surface 14, and associate stabilizer 54 with skull bone 19. Thereafter, the user may push on handle 58 such that lever 56 is pushed downwards, which in turn generates a torque that lifts cranial drill guard 10 from skull bone 19.

In another embodiment illustrated in FIGS. 3A-3C, the methods of the present disclosure include placing cranial drill guard 60 on skull bone 19 of a subject; attaching the plurality of protruding helical ridges 70 to skull bone 19 by screwing cranial drill guard 60 onto the skull bone; inserting cranial drill bit 11 into cavity 74 of cranial drill guard 60; and actuating the cranial drill bit to perforate the skull bone. Advantageously, the penetration of cranial drill bit 11 into skull bone 19 stops automatically once cranial drill bit 11 reaches the end of skull bone 19. In some embodiments, the automatic stopping may be actuated by proximal surface 64. Additionally, aperture 78 dispenses skull bone components (e.g., skull bone fragments and/or skull bone dust), allows irrigation during drilling, mitigates overheating of cranial drill bit 11 and cranial drill guard 60 during drilling, and/or mitigates jamming of the cranial drill bit 11 and cranial drill guard 60.

In some embodiments, the attachment step may also include attaching the plurality of serrations 71 onto skull bone 19 by tapping cranial drill guard 60 onto the skull bone, such as by a lightweight mallet. In some embodiments, such an attachment step may occur prior to attaching the plurality of protruding helical ridges 70 to skull bone 19 by screwing cranial drill guard 60 onto the skull bone.

In some embodiments, the attachment of the plurality of protruding helical ridges 70 to skull bone 19 occurs through the utilization of guard actuator 80 (illustrated in FIG. 3C). For instance, a user may grasp guard actuator 80 through handle 86, place grasper 82 around proximal surface 64, and screw in cranial drill guard 60 into skull bone 19 by rotating guard actuator 84.

In some embodiments, cranial drill guard 60 may also be removed from skull bone 19 after the perforation is completed through the utilization of guard actuator 80. For instance, a user may grasp guard actuator 80 through handle 86, place grasper 82 around proximal surface 64, and screw cranial drill guard 60 out of skull bone 19 by rotating guard actuator 84.

The methods of the present disclosure can include numerous embodiments. For instance, in preferred embodiments, a subject's head is fixed either to a skull clamp or taped to an operating room table during perforation. In further preferred embodiments, the cranial drill guard is fixed tightly to a skull bone and the functionality of the cranial drill bit is checked before a procedure. In further preferred embodiments, the subject is placed under local or general anesthesia (depending on the planned operation).

In some embodiments, an operator of a cranial drill guard may first make a small (e.g., 25 mm) incision on the scalp of the subject. Thereafter, the operator may place a small skin retractor (e.g., a Weitlaner skin retractor) on the scalp to expose the skull bone.

Next, the operator checks the cranial drill and its corresponding drill bit for functionality. For instance, an operator may be in standing position with feet apart for stability.

Thereafter, the operator then pushes aside the pericranium and exposes the periosteum. At this time, the operator may attach a cranial drill guard of the present disclosure to the skull bone.

In preferred embodiments, the operator uses both hands to steady the drill, drill bit and cranial drill guard prior to the commencement of drilling. In further preferred embodiments, an assistant may irrigate the resulting bone dust and clear the bone dust to prevent the drill from over-heating and jamming.

In preferred embodiments, the operator makes every effort to maintain the perpendicular axis of the drill with respect to the skull bone. In further preferred embodiments, the operator does not rotate the drill while drilling. Moreover, the operator does not remove the drill to periodically check skull bone depth. Under these strict guidelines, the self-release drill bit may automatically stop upon contact with the dura matter.

Applications and Advantages

The cranial drill guards and methods of the present disclosure provide numerous advantages. For instance, in some embodiments, the cranial drill guards of the present disclosure are in the form of a safe, single, compact, scalable, cost-effective, reusable, and integrated unit without any moving parts. Moreover, the methods of the present disclosure can utilize the cranial drill guards of the present disclosure to perforate a skull bone of a subject in a one-step procedure that is safe and effective. Additionally, due to their compact and single-unit nature, the cranial drill guards of the present disclosure can be mass manufactured in a cost effective and expedited manner.

As such, in some embodiments, the methods and cranial drill guards of the present disclosure can be used to safely maintain the stability of a cranial drill bit, thereby enabling the creation of a perfect and even cut of both outer and inner tables of a skull bone without plunging or creating imperfect perforations.

Additionally, the cranial drill guards and methods of the present disclosure may be used to minimize neurosurgeon anxiety during craniotomy. The cranial drill guards and methods of the present disclosure may also reduce the number of surgical complications due to plunging, thereby maximizing patient safety while minimizing patient costs and legal liability of health care providers and healthcare institutions.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A cranial drill guard operational for performing craniotomy, wherein the cranial drill guard comprises:
    a proximal end comprising a proximal surface, wherein the proximal end is operational to receive the cranial drill bit;
    a distal end comprising a distal surface operational to interface with a skull bone, and a plurality of protruding ridges for attachment to the skull bone;
    a wall extending from the proximal end to the distal end; and
    a cavity within the wall, wherein the cavity extends longitudinally from the proximal end to the distal end, and wherein the cavity is operational to stabilize, guard, and avoid lateral movement of the cranial drill bit during craniotomy.

2. The cranial drill guard of claim 1, wherein the diameter of the proximal surface is larger than the diameter of the cavity, and wherein the proximal surface is operational to guide the cranial drill bit into the cavity while guarding the cranial drill bit from over-penetration, under-penetration, or incomplete perforation into a subject's skull bone.

3. The cranial drill guard of claim 1, wherein the diameter of the distal surface is larger than the diameter of the cavity.

4. The cranial drill guard of claim 1, wherein the distal surface comprises a concave surface.

5. The cranial drill guard of claim 1, wherein the plurality of protruding ridges protrude out of the distal surface.

6. The cranial drill guard of claim 1, wherein the plurality of protruding ridges are in the form of a plurality of protruding spikes.

7. The cranial drill guard of claim 6, wherein the plurality of protruding spikes protrude out of the distal surface.

8. The cranial drill guard of claim 1, wherein the plurality of protruding ridges are in the form of a plurality of protruding helical ridges.

9. The cranial drill guard of claim 8, wherein the plurality of protruding helical ridges protrude out of the wall of the distal end.

10. The cranial drill guard of claim 8, wherein the plurality of protruding helical ridges are in the form of threads, ultrathin threads, serrations, screws, or combinations thereof.

11. The cranial drill guard of claim 1, wherein the wall comprises one or more apertures that extend through the wall.

12. The cranial drill guard of claim 1, wherein the wall is in the shape of a cylinder.

13. The cranial drill guard of claim 1, wherein the cavity has the same diameter from the proximal end to the distal end.

14. The cranial drill guard of claim 1, wherein the distance between the proximal end and distal end is less than about 60 mm.

15. The cranial drill guard of claim 1, wherein the ratio of the distance between the proximal end and distal end and the cavity diameter is less than 5.

16. A method of performing craniotomy on a skull bone of a cranium of a subject, said method comprising:
placing a cranial drill guard on a surface of the skull bone of the subject, wherein the cranial drill guard is suitable for use in performing craniotomy and operational for stabilizing a cranial drill bit, and wherein the cranial drill guard comprises:
a proximal end comprising a proximal surface, wherein the proximal end is operational to receive the cranial drill bit;
a distal end comprising a distal surface operational to interface with the skull bone, and a plurality of protruding ridges for attachment into the skull bone;
a wall extending from the proximal end to the distal end; and
a cavity within the wall, wherein the cavity extends longitudinally from the proximal end to the distal end, and wherein the cavity is operational to stabilize, guard, and avoid lateral movement of the cranial drill bit;
attaching the plurality of protruding ridges of the cranial drill guard into the skull bone of the subject;
inserting the cranial drill bit into the cavity of the cranial drill guard; and
actuating the cranial drill bit to perforate the skull bone, wherein the cavity guards, stabilizes, and avoids lateral movement of the cranial drill bit during the actuating.

17. The method of claim 16, wherein the plurality of protruding ridges are in the form of a plurality of protruding spikes, and wherein the attaching comprises pushing the plurality of spikes into the skull bone of the subject.

18. The method of claim 16, wherein the plurality of protruding ridges are in the form of a plurality of protruding helical ridges, and wherein the attaching comprises screwing the plurality of protruding helical ridges into the skull bone of the subject.

19. The method of claim 16, wherein the diameter of the proximal surface is larger than the diameter of the cavity, and wherein the proximal surface guides the cranial drill bit into the cavity while guarding the cranial drill bit from over-penetration, under-penetration, or incomplete perforation into the subject's skull bone.

20. The method of claim 16, wherein the distal surface comprises a concave surface that is operational to interface with convex areas of the skull bone.

21. The method of claim 16, wherein the wall comprises one or more apertures that extend through the wall, wherein the one or more apertures are operational to at least dispense skull bone components, allow irrigation during drilling, mitigate overheating of the cranial drill bit and cranial drill guard, mitigate jamming of the cranial drill bit and cranial drill guard, or combinations thereof.

22. The method of claim 16, wherein the cranial drill guard maintains a perpendicular position of the cranial drill bit.

23. The method of claim 16, wherein the distance between the proximal end and distal end is less than about 60 mm.

24. The method of claim 16, wherein the ratio of the distance between the proximal end and distal end and the cavity diameter is less than 5.

25. The method of claim 16, further comprising a step of removing the cranial drill guard from the skull bone, wherein the removing occurs after the craniotomy.

* * * * *